United States Patent [19]

Hammen et al.

[11] Patent Number: 5,043,471

[45] Date of Patent: Aug. 27, 1991

[54] PROCESS FOR THE PREPARATION OF POLYISOCYANATES

[75] Inventors: Günter Hammen, Rommerskirchen; Hartmut Knöfel, Odenthal-Erberich; Wolfgang Friederichs, Cologne, all of Fed. Rep. of Germany

[73] Assignee: Bayer Aktiengesellschaft, Bayerwerk, Fed. Rep. of Germany

[21] Appl. No.: 519,190

[22] Filed: May 4, 1990

[30] Foreign Application Priority Data

May 10, 1989 [DE] Fed. Rep. of Germany ....... 3915181

[51] Int. Cl.$^5$ ............................................. C07C 263/00
[52] U.S. Cl. ................................................... 560/345
[58] Field of Search ........................................ 560/345

[56] References Cited

U.S. PATENT DOCUMENTS

| | | |
|---|---|---|
| 2,409,712 | 10/1946 | Schweitzer. |
| 3,919,278 | 11/1975 | Rosenthal et al.. |
| 3,919,279 | 11/1975 | Rosenthal et al.. |
| 3,962,302 | 6/1976 | Rosenthal et al.. |
| 4,081,472 | 3/1978 | Tsumura et al.. |
| 4,330,479 | 5/1982 | Merger et al.. |
| 4,388,246 | 6/1983 | Sundermann et al.. |
| 4,692,550 | 9/1987 | Engbert et al.. |

FOREIGN PATENT DOCUMENTS 0231640 11/1985 Japan ................................. 560/345

*Primary Examiner*—Alan Siegel

*Attorney, Agent, or Firm*—Joseph C. Gil; Richard E. L. Henderson; Godfried R. Akorli

[57] ABSTRACT

The present invention relates to a process for the preparation of a polyisocyanate comprising
(a) thermally decomposing in a tube reactor a solution of an N-substituted carbamic acid ester corresponding to said polyisocyanate in a solvent used as decompositoin medium, wherein said solvent (i) is capable of dissolving the carbamic acid ester, (ii) is stable at the decomposition temperature and chemically inert towards the carbamic acid esters and the polyisocyanate product, (iii) can be distilled without decomposing under the conditions of decomposition of carbamic acid estes, and (iv) has at least one miscibility gap with an extracting agent used according to the extraction step (c), said solutions being carried along the internal wall of reactor;
(b) separating the gaseous materials formed in the tube reactor by fractional condensation into a fraction I comprised mainly of the alcohol by-product and a fraction II comprised mainly of polyisocyanates, isocyanatourethanes, unreacted carbamic acid ester, and the solvent used in step (a);
(c) extracting the polyisocyanate from said fraction II with an extracting agent that is at least partly immiscible with the decomposition medium and is a solvent for the polyisocyanate, and optionally distilling the resultant solution of the polyisocyanate in the extracting agent; and
(d) recycling the portion of fraction II remaining after the polyisocyanate is extracted.

8 Claims, No Drawings

PROCESS FOR THE PREPARATION OF POLYISOCYANATES

BACKGROUND OF THE INVENTION

This invention relates to a novel process for the preparation of organic polyisocyanates by thermal decomposition of the corresponding carbamic acid esters upon which the polyisocyanates are based.

It has long been known that N-substituted urethanes can be thermally decomposed in the gaseous or the liquid phase into isocyanates and alcohol. For example, A. W. Hofmann, *Ber. Dtsch. Chem. Ges.*, 3, 653 (1870); and H. Schiff, *Ber. Dtsch. Chem. Ges.*, 3, 649 (1870).

U.S. Pat. No. 2,409,712 discloses a process in which recombination of the products obtained from the solvent-free decomposition of carbamic acid esters can be prevented by introducing the products into a cyclohexane-water mixture. This process, however, provides only moderate isocyanate yields because of the partial hydrolysis of the resulting isocyanate at the phase interface.

The processes according to U.S. Pat. Nos. 3,962,302 and 3,919,278, for example, take place in the presence of inert high boiling solvents. In these processes, the two products of decomposition, that is, the alcohol and the isocyanate, are together continuously distilled from the decomposition medium and separated by fractional condensation. The disadvantages of these processes lie in the considerable technical expenditure required for the separation of the alcohol and isocyanate vapors and the moderate yields obtained. Readily volatile isocyanates are difficult to remove from the decomposition medium by distillation because of the high dilution and consequent low partial vapor pressure.

In the processes according to U.S. Pat. No. 3,919,279, German Offenlegungsschrift 2,635,490 or German Offenlegungsschrift 2,942,543, homogeneous or heterogeneous catalysts are used for increasing the volume/time yields. According to European Application 61,013, secondary isocyanate reactions are suppressed by the addition of stabilizing additives, but such additives cannot reduce the difficulties encountered in the required distillation of the isocyanates.

According to European Application 92,738, secondary isocyanate reactions may be suppressed by keeping the dwell time short. To achieve this, the molten carbamic acid ester is carried along the internal wall of a tube reactor in the presence of small quantities of an auxiliary solvent. The high boiling by-products, as well as the auxiliary solvent, are discharged as sump product, whereas the decomposition gases consisting of isocyanate and alcohol are removed at the top and separated by fractional condensation. Because only small quantities of auxiliary solvents are employed in this process, so that the carbamic acid ester is subjected to thermolysis in a virtually undiluted state, the formation of highly viscous polymeric by-products cannot be avoided. Moreover, the isocyanate removed at the top is invariably contaminated with carbamic acid esters caused by partial recombination with the alcohol that is also removed at the top.

An object of the present invention is to provide a process for the preparation of organic polyisocyanates by thermal decomposition of the carbamic acid esters corresponding to the desired polyisocyanates, whereby the polyisocyanates can be obtained without the formation of by-products and without recombination with the alcohol formed in the process. This object has been accomplished by the process of the invention described below.

SUMMARY OF THE INVENTION

The present invention relates to a process for the preparation of a polyisocyanate comprising (a) thermally decomposing in a tube reactor at temperatures above about 150° C. a solution of at least 25% by weight of an N-substituted carbamic acid ester corresponding to said polyisocyanate in up to 75% by weight of a solvent or solvent mixture serving as a decomposition medium, wherein said solvent or solvent mixture (i) is capable of dissolving the carbamic acid ester, (ii) is stable at the decomposition temperature and chemically inert towards the carbamic acid esters and the polyisocyanate formed during the decomposition reaction, (iii) can be distilled without decomposing under the conditions of decompositon of carbamic acid esters, and (iv) has at least one miscibility gap with an extracting agent used according to the extraction step (c), said solutions being carried along the internal wall of said reactor, to produce mixtures of polyisocyanates, isocyanatourethanes, and the unreacted carbamic acid ester (the quantity of said polyisocyanate preferably being at least 50% of the theoretical value);

(b) separating the gaseous materials formed in the tube reactor by fractional condensation into a fraction I comprised mainly of the alcohol produced by thermal decomposition of the carbamic acid ester and a fraction II comprised mainly of polyisocyanates, isocyanatourethanes, unreacted carbamic acid ester, and the solvent or solvent mixture used in the decomposition step (a);

(c) extracting the polyisocyanate from said fraction II with an extracting agent, wherein said extracting agent is at least partly immiscible with the decomposition medium and is a solvent for the polyisocyanate, and optionally distilling the resultant solution of the polyisocyanate in the extracting agent, thereby yielding the polyisocyanate in substantially purified form; and (d) recycling the portion of fraction II remaining after the polyisocyanate is extracted in extraction step (c) (preferably by addition to the decomposition step (a)).

In a preferred embodiment, the solvent or solvent mixture is a polar liquid having a dielectric constant at 25° C. greater than 20 and a boiling point at least 10° C. greater than the boiling point of the alcohol into which the carbamic acid ester decomposes. In a more preferred embodiment, the solvent is sulfolane or 3-methylsulfolane.

Preferred extracting agents are solvents having a boiling point or boiling range of from about 30° C. to about 200° C. at 1013 mbar and selected from aliphatic, cycloaliphatic, or araliphatic hydrocarbons; aliphatic ethers; or any mixtures of such solvents. Particularly preferred extracting agents include isooctane, cyclohexane, toluene, and/or tert-butyl methyl ether.

DETAILED DESCRIPTION OF THE INVENTION

The carbamic acid esters used in the process according to the invention are compounds or mixtures of compounds corresponding to the formula $$R^1(NHCOOR^2)_n$$

wherein $R^1$ is an aliphatic hydrocarbon containing about 4 to about 18 carbon atoms and optionally containing inert substituents, a cycloaliphatic hydrocarbon group containing about 6 to about 25 carbon atoms and optionally containing inert substituents, an araliphatic hydrocarbon group containing 7 to about 25 carbon atoms and optionally containing inert substituents, or an aromatic hydrocarbon group containing 6 to about 30 carbon atoms and optionally containing inert substituents;

$R^2$ is an aliphatic hydrocarbon group containing 1 to about 18 carbon atoms, a cycloaliphatic hydrocarbon group containing 5 to about 15 carbon atoms, an araliphatic hydrocarbon group containing 7 to about 10 carbon atoms, or an aromatic hydrocarbon group containing 6 to about 10 carbon atoms; and n is an integer of from 2 to about 5, with the proviso that the alcohols $R^2$-OH corresponding to group $R^2$ have boiling points at atmospheric pressure at least 10° C. lower than the boiling point of the solvent used and the boiling point of the polyisocyanate $R^1(NCO)_n$ corresponding to group $R^1$.

The preferred carbamic acid esters of the above formula used for the process according to the invention are those wherein $R^1$ is an aliphatic hydrocarbon group containing 4 to 12 (more preferably 6 to 10) carbon atoms, a cycloaliphatic hydrocarbon group containing 6 to 15 carbon atoms, a xylylene group, or an aromatic hydrocarbon group containing a total of 7 to 30 carbon atoms and optionally carrying methyl substituents and/or methylene bridges;

$R^2$ is an aliphatic hydrocarbon group containing 1 to 6 (preferably 1 to 4) carbon atoms, a cyclohexyl group, or a phenyl group; and n is from 2 to 5.

Examples of suitable carbamic acid esters include 1-(butoxycarbonylamino)-3,3,5-trimethyl-5-(butoxycarbonylaminomethyl)cyclohexane, 1-methyl-2,4-bis(ethoxycarbonylamino)benzene, 1-methyl-2,6-bis(ethoxycarbonylamino)benzene, 1,10-bis(methoxycarbonylamino)decane, 1,12-bis(butoxycarbonylamino)dodecane, 1,12-bis(methoxycarbonylamino)dodecane, 1,12-bis(phenoxycarbonylamino)dodecane, 1,18-bis(2-butoxyethylcarbonylamino)octadecane, 1,18-bis(benzoyloxycarbonylamino)octadecane, 1,3-bis[(ethoxycarbonylamino)methyl]benzene, 1,3-bis(methoxycarbonylamino)benzene, 1,3-bis[(methoxycarbonylamino)methyl]benzene, 1,3,6-tris(methoxycarbonylamino)hexane, 1,3,6-tris(phenoxycarbonylamino)hexane, 1,4-bis[(3-isopropyl-5-methylphenoxy)carbonylamino]butane, 1,4-bis(ethoxycarbonylamino)butane, 1,4-bis(ethoxycarbonylamino)cyclohexane, 1,5-bis(butoxycarbonylamino)naphthalene, 1,6-bis(ethoxycarbonylamino)hexane, 1,6-bis(methoxycarbonylamino)hexane, 1,6-bis(methoxymethylcarbonylamino)hexane, 1,8-bis(ethoxycarbonylamino)octane, 1,8-bis(phenoxycarbonylamino)-4-(phenoxycarbonylaminomethyl)octane, 2,2'-bis(4-propoxycarbonylaminophenyl)propane, 2,2'-bis(methoxycarbonylamino)diethyl ether, 2,4'-bis(ethoxycarbonylamino)diphenylmethane, 2,4-bis(methoxycarbonylamino)cyclohexane, 4,4'-bis(ethoxycarbonylamino)diphenylmethane, 2,4'-bis(ethoxycarbonylamino)diphenylmethane, 4,4'-bis(methoxycarbonylamino)-2,2-dicyclohexylpropane, 4,4'-bis(methoxycarbonylamino)biphenyl, 4,4'-bis(butoxycarbonylamino)-2,2-dicyclohexylpropane, 4,4'-bis(phenoxycarbonylamino)dicyclohexylmethan, and 4,4'-bis(phenoxycarbonylamino)diphenylmethane.

Suitable solvents for use as the reaction media for carrying out the process of the invention, include polar solvents having a boiling point at least 10° C. higher than the alcohol released from the carbamic acid ester under the decomposition conditions of the process and must also satisfy the following requirements. Suitable solvents must dissolve both the carbamic acid ester starting materials and the isocyanate reaction products under the conditions of the extraction method described below, must be substantially stable to heat under the decomposition conditions, must be chemically inert towards the carbamic acid esters used in the process and the isocyanates formed in the process, and must have at least one miscibility gap with the extracting agent used in the extraction step of the process of the invention.

Examples of solvents which conform to these criteria and are suitable as the reaction media for the process of the invention include aliphatic sulfones, such as diethyl sulfone, dipropyl sulfone, dibutyl sulfone, and ethyl propyl sulfone; cyclic sulfones, such as sulfolane, 2-methylsulfolane, 3-methylsulfolane, and 2,4-dimethylsulfolane; araliphatic sulfones, such as methyl phenyl sulfone and ethyl phenyl sulfone; aromatic sulfones, such as diphenyl sulfone and 4-methylphenyl phenyl sulfone; aromatic nitro compounds, such as nitrobenzene, 2-nitrotoluene, 3-nitrotoluene, and 4-chloronitrobenzene; and mixtures of such compounds. Preferred solvents include sulfolane, 3-methyl sulfolane, and nitrobenzene, particularly sulfolane.

Suitable extracting agents include, in particular, aliphatic and cycloaliphatic hydrocarbons and aliphatic ethers having a boiling point or boiling range of from about 30° to about 200° C. (preferably from 30° to 150° C.) at 1013 mbar. Examples of suitable extracting agents include hexane, isooctane, petroleum hydrocarbon fractions conforming to the above definitions, cyclohexane, methylcyclohexane, and aliphatic ethers containing at least 4 (preferably 4 to 12) carbon atoms, such as diethyl ether, isomeric butyl ethers, tert-butyl methyl ether, and heptyl methyl ether. Aromatic hydrocarbons such as benzene, toluene, and xylene are also suitable but less preferred. The aliphatic and cycloaliphatic hydrocarbons exemplified above are particularly preferred extracting agents. Any mixtures of the extracting agents exemplified above may, of course, also be used.

The process according to the invention may be carried out according to following general method. Generally, a solution containing at least 25% by weight (preferably not less than 40% by weight) of the carbamic acid ester in a solvent or solvent mixture of the type described above serving as reaction medium, and optionally containing up to 10 mole % (preferably up to 1 mole %) of a catalyst, is passed as a thin layer along the internal wall of a tube heated to about 150° to about 400° C. under a pressure of from 0.001 to 5 bar. The residence time of the carbamic acid ester in the reaction tube is kept very short in order to suppress side reactions. The decomposition products are rapidly removed from the reaction zone as gaseous products, together with at least part of the solvent used, and are selectively condensed in two suitably heat-controlled dephlegmators (that is, cross flow cooling device) arranged in sequence so that two fractions are obtained, a fraction I comprised mainly of alcohol and a fraction II comprised mainly of isocyanate and solvent and possibly also containing isocyanatourethanes and/or carbamic acid esters arising from incomplete decomposition or recombination.

The construction of the tube reactor used for the process of the invention may vary considerably, provided the reactors can be operated in such a manner that the carbamic acid ester can be distributed as a thin layer over the heated internal wall of the tube and the gaseous and/or liquid decomposition products can be removed from the tube. Distribution of the carbamic acid esters over the internal wall of the tube may take place in vertically placed reaction tubes without the aid of special devices if the solution of the carbamic acid ester to be decomposed is applied uniformly over the tube wall by means of suitable devices, such as a nozzle. Distribution of the carbamic acid ester over the tube wall may also be carried out with the aid of a mechanical stirrer or similar devices, which are in most cases necessary if the tube reactor is not placed vertically.

The high boiling by-products, as well as a part of the solvent or solvent mixture serving as a decomposition medium, are discharged as sump product.

Stirrers used to produce or improve the liquid film may advantageously also be used to transport the material situated on the wall of the tube, either by inhibiting the downwardly directed flow of the film of liquid or, for obliquely placed or horizontal reactors, by conveying the solution of the carbamic acid ester and/or its decomposition products from the decomposition zone to the end of the tube.

Examples of suitable decomposition reactors include glass, quartz, or metal tubes operating as falling film evaporators; tube reactors fitted with screw type stirrers, optionally tapering at the end; and various forms of conventional thin-layer evaporators. Of these apparatuses, thin-layer evaporators equipped with mechanical stirrers are particularly effective.

The process according to the invention proceeds satisfactorily if the descending film of liquid is continuously depleted of the carbamic acid and little or no starting material remains at the end of the decomposition zone. The process of the invention for the thermal decomposition of carbamic acid esters may, of course, also be carried out in such a manner that the carbamic acid esters introduced are only incompletely decomposed, thereby giving a product consisting predominantly or at least partially of isocyanatourethanes and/or carbamic acid esters that are removed as fraction II.

Fraction II, which results from the thermal decomposition of carbamic acid esters and which contains mainly the polyisocyanates to be prepared but also residues of undecomposed or only partially decomposed carbamic acid esters, is subjected to extraction in a second step of the process of the invention. If desired, fraction II may, of course, previously be diluted with further solvents of the type mentioned above.

For carrying out the extraction of the invention, the isocyanate-containing fraction II is vigorously mixed with an extracting agent, as exemplified above, that is liquid at room temperature. This extracting agent is used in about 0.1 to about 25 (preferably 0.5 to 5) times the quantity by weight of fraction II to be extracted. Fraction II is generally mixed with the extracting agent within a temperature range of from about $-20°$ C. to about 150° C. (preferably from 10° C. to 100° C.). This procedure generally results in the spontaneous formation of a diphasic mixture of two liquid phases which, after phase deposition, can be separated into an upper phase and a lower phase. The formation of a diphasic system may in special cases be promoted by cooling the mixture of fraction II and the extracting agent. Thus, for example, mixing can be carried out at about 70° C. to 100° C. and the resultant mixture may then be cooled to a lower temperature, for example, in the range of from 10° C. to 40° C.

The upper phase of the diphasic system generally constitutes the main phase and the lower phase the secondary phase, although the ratio by volume depends to a large extent on the quantity of extracting agent used. In the process of the invention, phase separation may be carried out by known methods, for example, by discharging the lower phase, by decanting, by siphoning, or by other suitable methods of phase separation. Part of the polyisocyanate that is to be recovered in pure form is then present in the upper main phase. Other components of the upper phase include part of the solvent used as decomposition medium and the major proportion of the extracting agent used. The lower phase consists mainly of the solvent used as decomposition medium, the unreacted or only partially reacted carbamic acid esters, and that part of the polyisocyanate product that has not been transferred into the upper phase. To obtain this part of the polyisocyanate in pure form, the lower phase may be subjected to one or more additional extractions carried out in the manner described.

In a preferred embodiment of the process of the invention, mixing fraction II with the extracting agent and subsequent phase separation (that is, extraction of fraction II) are carried out continuously using conventional continuously operating counterflow extraction apparatus.

The extraction gives rise to one or more upper extraction phases containing the polyisocyanate and a generally homogeneous second phase mainly containing unreacted or only incompletely reacted carbamic acid ester. Multiple upper extracts can optionally be combined. The lower phase may be reused as solvent for the decomposition reaction.

To obtain the poklyisocyanates in the pure form, the upper extraction phases are worked up by distillation, the extracting agent generally constituting the first fraction to be removed by distillation. Separation of the polyisocyanates from residual solvent used as the decomposition medium may also be carried ou by distillation, during which the polyisocyanate or the solvent used as the decomposition medium forms the distillation residue. It is generally preferred to use decomposition solvents having a clearly different boiling point from that of the polyisocyanate product so that the two can easily be separated. When the upper extraction phases are worked up by distillation, the polyisocyanate generally constitutes the distillation residue. Workup by distillation can also be carried out continuously using known distillation apparatus. If desired, polyisocyanates obtained as distillation residue can be subjected to a further, fine distillation, but even without such fine distillation the polyisocyanates obtained as distillation residues can sometimes have a purity of greater than 90% by weight.

It is a particular advantage of the process of the invention that the polyisocyanates obtained from the decomposition reaction are rapidly removed from the reaction zone as dilute gaseous products and are therefore subjected only to mild thermal conditions. Furthermore, the isocyanatourethanes formed as the result of recombination with the alcohol that is simultaneously distilled off are also separated under the mild conditions used during extraction. As a result, the known secondary reactions of isocyanates, which can in some cases be catalyzed by the carbamic acid esters used in the process, are to a large extent suppressed. Thus, a substantially higher proportion of the polyisocyanate formed in the decomposition reaction remains undecomposed and may be isolated in pure form.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are molar percentages.

The "first cycle" yields are based on the actual yields obtained in the Examples. The "continuous process" yields refer to the total amount of diisocyanate obtained by (1) recovering additional diisocyanate from the first cycle and (2) converting unreacted and partially reacted carbamic acid ester to product in subsequent decomposition steps. This yield is calculated as the limiting value of a geometric row and is given by:

$$y = \frac{y_1}{1 - (s_1 - y_1)/100}$$

where
y = continuous process yield (%)
$y_1$ = first cycle yield (%)
$s_1$ = sum of total amount of diisocyanate and unreacted and partially reacted carbamic acid esters (%)

EXAMPLES

Unless otherwise indicated, the decomposition reactor for this procedure is a cylindrical thin-layer evaporator (effective length 300 mm and diameter 35 mm) equipped with a metal blade stirrer whose movable blades extend to the wall of the evaporator. A heatable addition funnel at the head of the thin-layer evaporator is used for introducing the carbamic acid ester to be decomposed. Reaction products which cannot be evaporated are discharged through a closable tap at the bottom of the thin-layer evaporator. Components of the reaction mixture which can be evaporated are removed through a heated transverse flow condenser placed at the head of the thin-layer evaporator and having two sequentially arranged condensation coils, each of which has a discharge outlet. Evacuation of the decomposition apparatus is carried out using a rotary disk pump with a cooling trap behind the condensation coil.

The isocyanate-containing condensate obtained as fraction II in the decomposition reaction is warmed to a temperature suitable for extraction, optionally after the addition of further solvent, and is extracted in a heatable flask having a discharge at the bottom and equipped with a glass-covered paddle stirrer, a thermometer, and a reflux condenser.

Fraction II is mixed with the extracting agent and the mixture is vigorously stirred for 30 minutes. After the mixture has been allowed to stand for 10 minutes, the resulting two phases are separated. In some examples, the lower phase is subjected to one or more further extractions with fresh extracting agent. The upper phases are combined and then tested for their composition by means of high performance liquid chromatography ("HPLC"), as are the lower phases left over after extraction.

The abbreviation suffixes used below have the following meanings: "DI" denotes polyisocyanates free from urethane, in particular diisocyanate; "IU" denotes partially product containing urethane and isocyanate groups, in particular isocyanatourethane; and "DU" denotes unchanged starting material, in particular diurethane.

EXAMPLE 1

A solution of 285 g of 4,4'-bis(ethoxycarbonylamino)-diphenylmethane ("MDU") and 0.72 g of dibutyltin dilaurate in 300 g of sulfolane is introduced over a period of 5 hours (dripping rate of 120 g/h) from an addition funnel which is thermostatically controlled at 100° C. into a thin-layer evaporator which is heated to 270° C. The transverse flow condenser at the head of the apparatus is thermostatically controlled at 200° C. and the two condensation coils are thermostatically controlled at 50° C. and −20° C., respectively. The pressure in the apparatus during the decomposition reaction is 4 mbar. The gaseous mixture escaping at the top is fractionally condensed in the two condensation coils to yield 85 g of fraction I (composition: 74% by weight ethanol and 26% by weight sulfolane) and 500 g of fraction II (composition: 55.1% by weight sulfolane and 28.1% by weight 4,4'-diisocyanatodiphenylmethane ("MDI"), 13.5% by weight 4-ethoxycarbonylamino-4'-isocyanatodiphenylmethane ("MIU"), and 3.3% by weight MDU). Fraction II is extracted at room temperature four times each with 500 g portions of cyclohexane. According to the HPLC, the sulfolane phase contains 45.8 g of MDI, 55.2 g of MIU, and 14.5 g of MDU after the last extraction. The combined extracts contain a total of 79.8 g of MDI and 4.5 g of MIU. The MDU content is below the limits of detection. The isolable yields of 4,4'-diisocyanatodiphenylmethane calculated from these figures are 38.7% after a first cycle and 80.3% for a continuous process.

EXAMPLE 2

A solution of 290 g of 4,4'-bis(ethoxycarbonylamino)-diphenylmethane ("MDU") and 0.76 g of dibutyltin dilaurate in 300 g of sulfolane is thermolyzed as described in Example 1 over a period of 6 hours (dripping rate of 100 g/h) in a thin-layer evaporator heated with a heat carrying oil at 270° C. Yields of 66 g of fraction I (composition: 94% by weight ethanol and 6% by weight sulfolane) and 510 g of fraction II (composition: 59.9% by weight sulfolane and 25.2% by weight MDI, 11.8% by weight MIU, and 3.1% by weight MDU) are obtained. After fraction II is extracted four times each with 500 g portions of cyclohexane at 50° C., the sulfolane phase contains 24.0 g of MDI, 46.2 g of MIU, and 16.1 g of MDU. The combined extracts contain a total of 114.8 g of MDI and 11.2 g of MIU. The MDU content is below the limits of detection. The isolable yields of 4,4'-diisocyanatodiphenylmethane calculated from these figures are 54.1% after a first cycle and 90.0% for a continuous process.

EXAMPLE 3

A solution of 255 g of 2,4-bis(ethoxycarbonylamino)-toluene ("TDU") and 0.69 g of dibutyltin dilaurate in 75 g of sulfolane is thermolyzed as described in Example 1 over a period of 5.5 hours (dripping rate of 65 g/h) in a thin-layer evaporator heated with a heat carrying oil at 270° C. The transverse flow condenser at the head of the apparatus is thermostatically controlled at 150° C. and the two condensation coils are thermostatically controlled at 30° C. and −10° C., respectively. The pressure in the apparatus during the decomposition reaction is 10 mbar. Yields of 67 g of fraction I (composition: 96% by weight ethanol and 4% by weight of sulfolane) and 255 g of fraction II (composition: 34.9% by weight sulfolane and 23.2% by weight 2,4-diisocyanatotoluene ("TDI"), 35.3% by weight of the corresponding ethoxycarbonylaminoisocyanatotoluene ("TIU") isomeric mixture, and 6.7% by weight TDU) are obtained. After the addition of 350 g of sulfolane, fraction II is extracted four times each with 200 g portions of a tert-butyl methyl ether isooctane mixture (1:2) at room-temperature. The combined extracts contains a total of 40.4 g of TDI and 20.2 g of the TIU isomeric mixture. The TDU content is below the limit of detection. When the extraction has been completed, the sulfolane phase contains 29.3 g of TDI, 72.4 g of the TIU isomeric mixture, and 17.3 g of TDU. The isolable yields of 2,4-diisocyanatotoluene calculated from these figures are 24.3% after a first cycle and 76.6% for a continuous process.

EXAMPLE 4

A mixture of 275 g of 1-(ethoxycarbonylamino)-3,3,5-trimethyl-5-(ethoxycarbonylaminomethyl)cyclohexane ("IPDU"), 0.70 g of dibutyltin dilaurate, and 15 g of sulfolane is introduced as described in Example 1 over a period of 5 hours (dripping rate of 60 g/h) from an addition funnel which is thermostatically controlled at 150° C. into a thin-layer evaporator heated with a heat carrying oil at 310° C. The transverse flow condenser at the head of the apparatus is thermostatically controlled at 150° C. and the two condensation coils are thermostatically controlled at 20° C. and −10° C., respectively. The pressure in the apparatus during the decomposition reaction is 12 mbar. Yields of 63 g of fraction I (composition: 94% by weight ethanol and 6% by weight sulfolane) and 193 g of fraction II (composition: 3.5% by weight sulfolane and 45.9% by weight 1-isocyanato-3,3,5-trimethyl-5-(isocyanatomethyl)cyclohexane ("IPDI") and 47.0% by weight of the corresponding (ethoxycarbonylamino) (isocyanatomethyl)-3,3,5-trimethylcyclohexane ("IPIU") isomeric mixture) are obtained. (The carbamic acid ester IPDU that has remained unchanged in the decomposition reaction is not detected in the HPLC analysis.) After the addition of 180 g of sulfolane, fraction II is extracted four times each with 360 g portions of isooctane at 90° C. When the extraction has been completed, the sulfolane phase contains 3.5 g of IPDI and 15.6 g of the IPIU isomeric mixture. The combined extracts contain a total of 82.5 g of IPDI and 63.3 g of the IPIU isomeric mixture. The isolable yields of 1-isocyanato-3,3,5-trimethyl-5-(isocyanatomethyl)cyclohexane calculated from these figures are 42.4% after a first cycle and 71.6% for a continuous process.

EXAMPLE 5

A solution of 240 g of 1,6-bis(ethoxycarbonylamino)-hexane ("HDU") and 0.66 g of dibutyltin dilaurate in 85 g of sulfolane is thermolyzed as described in Example 1 over a period of 4.5 hours (dripping rate of 70 g/h) in a thin-layer evaporator heated with a heat carrying oil at 270° C. The transverse flow condenser at the head of the apparatus is thermostatically controlled at 150° C. and the two condensation coils are thermostatically controlled at 20° C. and −10° C., respectively. The pressure in the apparatus during the decomposition reaction is 15 mbar. Yields of 75 g of fraction I (composition: 75% by weight ethanol and 25% by weight of sulfolane) and 245 g of fraction II (composition: 27.9% by weight sulfolane and 35.8% by weight 1,6-diisocyanatohexane ("HDI") and 36.6% by weight 1-ethoxycarbonylamino-6-isocyanatohexane ("HIU")) are obtained. (The carbamic acid ester HDU that has remained unchanged in the decomposition reaction is not detected in the HPLC analysis.) Fraction II is extracted four times each with 160 g portions of isooctane at 90° C. The combined extracts contain a total of 48.6 g of HDI and 27.6 g of HIU. After the extraction has been completed, the sulfolane phase contains 21.8 g of HDI and 45.1 g of HIU. The isolable yields of 1,6-bis(ethoxycarbonylamino)hexane calculated from these figures are 31.4% after a first cycle and 72.5% for a continuous process.

What is claimed is:

1. A process for the preparation of a polyisocyanate comprising
    (a) thermally decomposing in a tube reactor at temperatures above about 150° C. a solution of at least 25% by weight of an N-substituted carbamic acid ester corresponding to said polyisocyanate in up to 75% by weight of a solvent or solvent mixture serving as a decomposition medium, wherein said solvent or solvent mixture (i) is capable of dissolving the carbamic acid ester, (ii) is stable at the decomposition temperature and chemically inert towards the carbamic acid esters and the polyisocyanate formed during the decomposition reaction, (iii) can be distilled without decomposing under the conditions of decomposition (iv) has at least one miscibility gap with an extracting agent used according to the extraction step (c) and is a polar solvent having a dielectric constant at 25° C. greater than 20 and a boiling point at least 10° C. great than the boiling point of the alcohol into which the carbamic acid ester decomposes, said solutions being carried along the internal wall of said reactor, to produce mixtures of polyisocyanates, isocyanatourethanes, and the unreacted carbamic acid ester;
    (b) separating the gaseous materials formed in the tube reactor by fractional condensation into a fraction I comprised mainly of the alcohol produced by thermal decomposition of the carbamic acid ester and a fraction II comprised mainly of polyisocyanates, isocyanatourethanes, unreacted carbamic acid ester, and the solvent or solvent mixture used in the decomposition step (a);
    (c) extracting the polyisocyanate from said fraction II with an extracting agent, wherein said extracting agent is at least partly immiscible with the decomposition medium and is a solvent for the polyisocyanate, and optionally distilling the resultant solution of the polyisocyanate in the extracting agent, thereby yielding the polyisocyanate in substantially purified form; and (d) recycling the portion of fraction II remaining after the polyisocyanate is extracted in extraction step (c).

2. A process according to claim 1 wherein the portion of the decomposition medium remaining after the extraction step (c) is recycled by addition to the decomposition step (a).

3. A process according to claim 1 wherein the solvent or solvent mixture serving as a decomposition medium is sulfolane or 3-methylsulfolane.

4. A process according to claim 1 wherein the extracting agent is one or more solvents having a boiling point or boiling range of from 30° to 200° C. at 1013 mbar selected from the group consisting of aliphatic, cycloaliphatic, and araliphatic hydrocarbons, and aliphatic ethers.

5. A process according to claim 1 wherein the extracting agent is isooctane, cyclohexane, toluene, and/or tert-butyl methyl ether.

6. A process according to claim 1 for the preparation of a polyisocyanate comprising (a) thermally decomposing in a tube reactor at temperatures above about 150° C. a solution of at least 25% by weight of an N-substituted carbamic acid ester corresponding to said polyisocyanate in up to 75% by weight of sulfolane or 3-methylsulfolane, said solutions being carried along the internal wall of said reactor, to produce mixtures of polyisocyanates, isocyanatourethanes, and the unreacted carbamic acid ester;

(b) separating the gaseous materials formed in the tube reactor by fractional condensation into a fraction I comprised mainly of the alcohol produced by thermal decomposition of the carbamic acid ester and a fraction II comprised mainly of polyisocyanates, isocyanatourethanes, unreacted carbamic acid ester, and the solvent or solvent mixture used in the decomposition step (a);

(c) extracting the polyisocyanate from said fraction II with isooctane, cyclohexane, toluene, and/or tert-butyl methyl ether as extracting agent, and optionally distilling the resultant solutin of the polyisocyanate in the extracting agent, thereby yielding the polyisocyanate in substantially purified form; and (d) recycling the portion of fraction II remaining after the polyisocyanate is extracted in extraction step (c).

7. A process according to claim 1 wherein the N-substituted carbamic acid ester is a compound corresponding to the formula $$R^1(NHCOOR^2)_n$$

wherein $R^1$ is an aliphatic hydrocarbon containing 4 to 18 carbon atoms and optionally containing inert substituents, a cycloaliphatic hydrocarbon group containing 6 to 25 carbon atoms and optionally containing inert substituents, an araliphatic hydrocarbon group containing 7 to 25 carbon atoms and optionally containing inert substituents, or an aromatic hydrocarbon group containing 6 to 30 carbon atoms and optionally containing inert substituents;

$R^2$ is an aliphatic hydrocarbon group containing 1 to 18 carbon atoms, a cycloaliphatic hydrocarbon group containing 5 to 15 carbon atoms, an araliphatic hydrocarbon group containing 7 to 10 carbon atoms, or an aromatic hydrocarbon group containing 6 to 10 carbon atoms; and n is an integer of from 2 to about 5, with the proviso that the alcohol $R^2$-OH corresponding to group $R^2$ has a boiling point at atmospheric pressure at least 10° C. lower than the boiling point of the solvent used as the decomposition medium and the boiling point of the polyisocyanate $R^1(NCO)_n$ corresponding to group $R^1$.

8. A process according to claim 7 wherein the N-substituted carbamic acid ester is a compound corresponding to the formula $$R^1(NHCOOR^2)_n$$

wherein $R^1$ is an aliphatic hydrocarbon group containing 4 to 12 carbon atoms, a cycloaliphatic hydrocarbon group containing 6 to 15 carbon atoms, a xylylene group, or an aromatic hydrocarbon group containing a total of 7 to 30 carbon atoms and optionally carrying methyl substituents and/or methylene bridges;

$R^2$ is an aliphatic hydrocarbon group containing 1 to 6 carbon atoms, a cyclohexyl group, or a phenyl group; and n is from 2 to 5.

* * * * *